(12) United States Patent
Abdel-Magid et al.

(10) Patent No.: US 6,258,956 B1
(45) Date of Patent: Jul. 10, 2001

(54) SYNTHESIS OF 3-AMINO-3-ARYL PROPANOATES

(75) Inventors: Ahmed F. Abdel-Magid, Ambler; Judith H. Cohen, North Wales; Cynthia A. Maryanoff, New Hope; Frank John Villani, Jr., Perkasie; Hua M. Zhong, Lansdale, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/532,799

(22) Filed: Mar. 21, 2000

Related U.S. Application Data

(60) Provisional application No. 60/125,669, filed on Mar. 22, 1999.

(51) Int. Cl.[7] .................. C07D 213/55; C07C 211/03; C07C 229/08
(52) U.S. Cl. .................. 546/335; 564/442; 560/37
(58) Field of Search .................. 546/335; 564/442; 560/37

(56) References Cited

U.S. PATENT DOCUMENTS

| 4,585,887 | 4/1986 | Jolidon et al. | 560/38 |
| 5,254,573 | * 10/1993 | Bovy et al. | 514/357 |
| 5,840,961 | 11/1998 | Behling et al. | 560/172 |

FOREIGN PATENT DOCUMENTS

| WO 97/41102 | 11/1997 | (WO) . |
| WO 98/02410 | 1/1998 | (WO) . |

OTHER PUBLICATIONS

Zhong et al, Tetrahedron Letters, vol. 40, pp. 7721–7725, Oct. 29, 1999.*

J.G. Rico, R.J. Lindmark, T.E. Rogers, & P.R. Bovy, A Highly Stereoselective Michael Addition to an a,β–Unsaturated Ester as the Crucial Step in the Synthesis of a Novel β–Amino Acid–Containing Fibrinogen Receptor Antagonist, J. Org. Chem. 1993, 58, 7948–7951.

F.A. Davis, J.M. Szewczyk & R.E. Reddy, An Efficient Synthesis of (S)—(+)—Ethyl β–Amino–3–pyridinepropanoate Using Enantiopure Sulfinimines, J. Org. Chem. 1996, 61, 2222–2225.

T.P. Tang & J.A. Ellman, The tert–Butanesulfinyl Group: An Ideal Chiral Directing Group and Boc–Surrogate for the Asymmetric Synthesis and Applications of β–Amino Acids, J. Org. Chem. 1999, 64, 12–13.

E. Wenkert, K. Orito, D. Simmons, J. Ardisson, N. Kunesch, & J. Poisson, An Alternate Synthesis of Deethylvincadifformine, J. Org. Chem., 1983, 48, 5006–5009.

J.K. Stille & P. K.Wong, Carboalkoxylation of Aryl and Benzyl Halides Catalyzed by Dichlorobis(triphenlyphosphine)palladium (II), J. Org. Chem., vol. 40, No. 4, 1975, 532–534.

A. Abdel–Magid, J. Cohen & C. Maryanoff, Chemical Process Synthesis of β–Amino Acids and Esters, Current Medicinal Chemistry, 1999, 6, 995–970.

V.M. Potapov, V.M. Demyanovich, T.V. Skvortsova, N.N. Melekhina, Synthesis and Configuraiton of (–) –α–) 3, 4–Dimethoxphenyl) Ethylamine, Vestnik Moskovskogo Universiteta, Chemistry, No. 4,1997, pp. 446–449 (translation enclosed).

* cited by examiner

Primary Examiner—Zinna Northington Davis
(74) Attorney, Agent, or Firm—Ellen Ciambrone Coletti

(57) ABSTRACT

A process for the synthesis of a compound of the formula

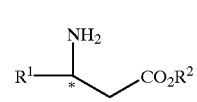

I wherein $R^1$ is aryl, heteroaryl, substituted aryl or substituted heteroaryl and $R^2$ is hydrogen, alkyl or aralkyl, or salt thereof.

21 Claims, No Drawings

SYNTHESIS OF 3-AMINO-3-ARYL PROPANOATES

CROSS REFERENCE TO OTHER APPLICATIONS

This application claims the benefit of U.S. Provisional Application No. 60/125,669, filed on Mar. 22, 1999.

FIELD OF THE INVENTION

BACKGROUND OF THE INVENTION

The invention relates to a process of preparing a compound of the formula

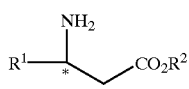

I wherein $R^1$ is aryl, heteroaryl, substituted aryl or substituted heteroaryl and $R^2$ is hydrogen, alkyl or aralkyl, or salt thereof.

Compounds of Formula I are useful as intermediates in the synthesis of, inter alia, compounds described in WO 97/41102. Compounds described in WO 97/41102 are antagonists of the platelet fibrinogen receptor (gp IIb/IIIa antagonist) and thus are useful for treating platelet-mediated thrombotic disorders such as arterial and venous thrombosis, acute myocardial infarction, reocclusion following thrombolytic therapy and angioplasty, inflammation, unstable angina and vaso-occlusive disorders.

Known methods for preparing compounds of Formula I include an asymmetric Michael addition of lithium (R)-N-(trimethylsilyl)-(1)-phenethylamide to ethyl 3-pyridyl acrylate to give the ethyl β-aminoester disclosed in U.S. Pat. No. 5,254,573. This process results in inefficient formation of lithium amide and difficult removal of N-(-methylbenzyl) group.

J. Org. Chem. vol. 61, p. 2222 (1996) discloses a process wherein the lithium enolate of ethyl acetate is added to an enantiomoric sulfinimine, the product of which is purified by chromatography and deprotected under acidic conditions to afford the β-amino ester in greater than 90% ee. The need for chromatographic purification makes this process unattractive for large-scale production.

WO 98/02410 discloses a process of stereoselective addition of the Reformatsky reagent prepared from t-butylbromoacetate to the enantiomeric imine prepared from 3-pyridine carboxaldehyde and (R)-2-phenylglycinol. Oxidative cleavage of the N-(1-phenyl-2-hydroxy ethyl) group with NaIO$_4$ in ethanol followed by acid hydrolysis affords the enantiomerically pure t-butyl β-amino ester. Use of oxidizing agents makes this process unattractive for large-scale production.

WO 97/41102 discloses enzymatic resolution of the (±)β-phenylacetamido acid using penicillin amidase to afford the S-acid. This process, which utilizes enzymes, is inefficient and impractical for large scale production.

Thus there exists a need for a process which is compatible with large scale production needs and which achieves acceptable levels of purity and yield.

BRIEF SUMMARY OF THE INVENTION

The invention relates to a process for preparing a compound of the formula

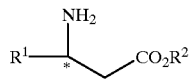

I wherein R1 is aryl, heteroaryl, substituted aryl or substituted heteroaryl and $R^2$ is hydrogen, alkyl or aralkyl, or salt thereof, comprising reacting a compound of the formula II

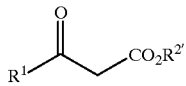

II wherein $R^1$ is as described above and $R^{2'}$ is alkyl or aralkyl, with a compound of the formula III

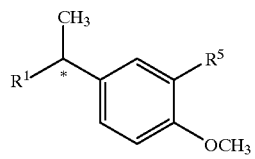

III wherein $R^5$ is hydrogen or alkoxy, under conditions of reduced pressure, such that the reaction solution boils at temperatures of between about 400 and about 65° C., in an inert solvent, which solvent under reduced pressure is capable of azeotropic removal of water, to form the compound of formula IV,

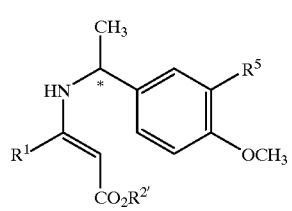

IV reacting the compound of formula IV with hydrogen gas in the presence of a palladium catalyst to form the compound of formula V

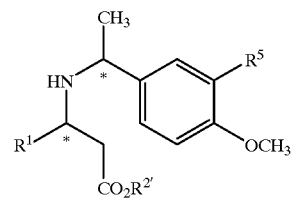

V and reacting the compound of formula V to form the compound of formula Ia or a salt thereof

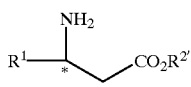

wherein $R^{2'}$ is alkyl or aralkyl.

If desired, compound Ia can further be converted to a compound of formula Ib or a salt thereof,

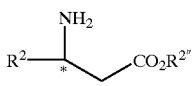

wherein $R^{2''}$ is hydrogen via saponification of the ester.

The process of this invention, as described herein, is advantageous over previously disclosed methods in that it is volume efficient, making it suitable for large scale production.

DETAILED DESCRIPTION OF THE INVENTION

As used herein, unless otherwise noted, alkyl whether used alone or as part of a substituent group, include straight and branched chains. For example, alkyl radicals include methyl, ethyl, n-propyl, isopropyl, n-butyl, isobutyl, sec-butyl, t-butyl, n-pentyl, n-hexyl and the like. Unless otherwise noted, "lower" when used with alkyl means a carbon-chain composition of 1–4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein alone or as part of a substituent group, unless otherwise noted, "aryl" shall refer to unsubstituted carbocylic aromatic groups such as phenyl, naphthyl, and the like. The aryl group may be substituted with at least one substituent. Suitable substituents on the aryl group are selected independently from the group consisting of halogen, hydroxy, lower alkyl, lower alkoxy, lower aralkyl, —$NR^3_2$, wherein $R^3$ is a lower alkyl; $R^4CONH$, wherein $R^4$ is phenyl or a lower alkyl; and —$OC(O)R^6$ wherein R6 is hydrogen, alkyl or aralkyl.

As used herein, unless otherwise noted, "heteroaryl" shall denote any five or six membered monocyclic aromatic ring structure containing at least one heteroatom selected from O, N and S or a bicyclic system wherein the monocyclic heteroaryl is fused to an aryl or monocyclic heteroaryl. Examples of suitable heteroaryl groups include, but are not limited to, pyrrolyl, pyridyl, pyrazinyl, pyrimidinyl, pyrazolyl, pyridazinyl, furanyl, pyranyl, imidazolyl, thienyl, oxazolyl, isothiazolyl, isoxazolyl, furazanyl, benzothienyl, benzofuranyl, indolyl, isoindolyl, indolizinyl, indazolyl, purinyl, isoquinolyl, quinolyl, isothiazolyl, and the like. The heteroaryl may be substituted with at least one substituent. Suitable substituents on the heteroaryl group are selected independently from the group consisting of halogen, hydroxy, lower alkyl, lower alkoxy, lower aralkyl, —$NR^3_2$, wherein $R^3$ is a lower alkyl; $R^4CONH$, wherein $R^4$ is phenyl or a lower alkyl, and —$OC(O)R^6$ wherein $R^6$ is hydrogen, alkyl or aralkyl; preferably halogen or lower alkyl. The heteroaryl group may be attached at any heteroatom or carbon atom of the ring such that the result is a stable structure. Preferably, the heteroaryl is selected from the group consisting of pyridyl, pyrimidinyl, furanyl and thienyl.

As used herein, unless otherwise noted, "aralkyl" shall mean any lower alkyl group substituted with an aryl group such as phenyl, naphthyl and the like.

As used herein, "halogen" shall mean chlorine, bromine, fluorine and iodine.

As used herein, the notation "*" shall denote the presence of a stereogenic center.

Compound of formula IV, because of the presence of a double bond, can exist in either the cis or the trans configuration or as a mixture of the two configurations.

Compound of formula V, because of the presence of two stereogenic centers can exist as any of four diastereomers, or mixture thereof.

As used herein, with respect to reagents and reaction products, the term "enantiomeric excess or ee" shall mean the excess amount of one enantiomer over another enantiomer. The enantiomeric excess (expressed as a percentage) is calculated as:

[(Amount Enantiomer$_{(1)}$–Amount Enantiomer$_{(2)}$)/(Total Amount Both Enantiomers)]*100%

Application of the present invention to a mixture of enantiomers of formula III, substantially free of the R enantiomer, will result in the production of a mixture of enantiomers of formula I, substantially free of the R enantiomer. Similarly, application of the present invention to a mixture of enantiomers of formula III, substantially free of the S enantiomer, will result in the production of a mixture of enantiomers of formula I, substantially free of the S enantiomer. Preferably, the enantiomeric excess of the desired enantiomer of formula III is at least 90 percent ee, more preferably at least 98 percent ee, most preferably 99 percent ee.

In a preferred embodiment of the invention, in the compound of formula I, $R^1$ is phenyl, pyrimidyl, unsubstituted or substituted pyridyl, napthyl or 3,5-dichlorophenyl, more preferably 2-pyridyl, 3-pyridyl or 4-pyridyl, most preferably 3-pyridyl. $R^2$ is preferably lower alkyl, more preferably methyl or ethyl.

The invention relates to a process for preparing a compound of the formula I

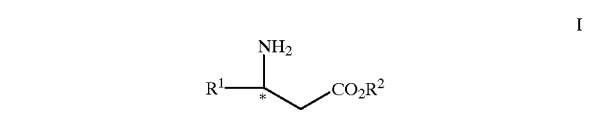

wherein $R^1$ is aryl, heteroaryl, substituted aryl or substituted heteroaryl and $R^2$ is hydrogen, alkyl or aralkyl, or salt thereof, comprising reacting a compound of the formula II

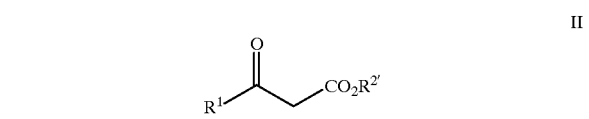

wherein $R^1$ is as described above and $R^{2'}$ is alkyl or aralkyl, with a compound of the formula III

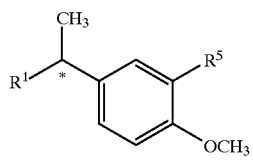

wherein $R^5$ is hydrogen or alkoxy, preferably hydrogen or methoxy, under conditions of reduced pressure, such that the reaction solution boils at temperatures of between about 40° and about 65° C., in an inert solvent, which solvent under reduced pressure is capable of azeotropic removal of water, to form the compound of formula IV

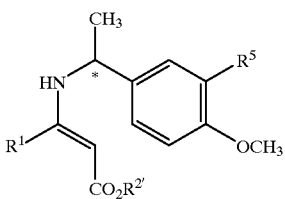

reacting the compound of formula IV with hydrogen gas in the presence of a palladium catalyst to form the compound of formula V

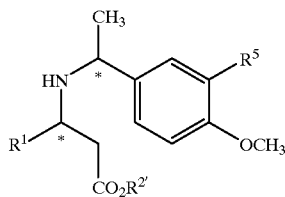

and reacting the compound of formula V to form the compound of formula Ia, wherein $R^2$ is alkyl or aralkyl or a salt thereof.

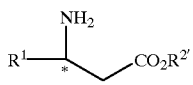

If desired, compound Ia can further be converted to a compound of formula Ib or a salt thereof, wherein $R^{2''}$ is hydrogen via saponification of the ester.

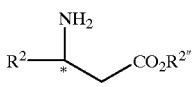

In accordance with the invention, a compound of formula II, a known compound or compound prepared by known methods, (*J. Org. Chem.* 1975, 40, 532; *J. Org. Chem.* 1983, 48, 5006) is reacted with a compound of formula III, a known compound or compound prepared by known methods, (*Vestn. Mosk. Univ. Ser2: Khim.* 1977, 18, 446; CAN 88:62074) in the presence of an acid, preferably a carboxylic acid, most preferably acetic acid, under vacuum, preferably the vacuum is adjusted so that the boiling point of the mixture is between about 40° and about 65° C. in an inert solvent, which solvent under reduced pressure is capable of azeotropic removal of water, such as xylene, heptane or toluene, preferably toluene, to form the compound of formula IV.

When the process is applied to a compound of formula II wherein $R^1$ is a nitrogen containing heteroaryl, the reaction is carried out in the presence of at least two equivalents of a carboxylic acid, preferably acetic acid.

Preferably, when $R^1$ is a N containing heteroaryl, the reaction solution is further washed with an aqueous base such as sodium bicarbonate, sodium carbonate and the like, to remove excess acid.

The compound of formula IV is reacted with hydrogen gas in the presence of a palladium catalyst such as palladium hydroxide on carbon, palladium on carbon and the like, preferably at least 10 weight percent of 20 percent palladium hydroxide on carbon, preferably under atmospheric pressure, in an alcohol solvent, such as lower alkyl alcohol, preferably methanol, preferably at from about 0° to about 40° C., most preferably at room temperature, to form the corresponding compound of formula V.

The desired diastereomer of formula V is preferably isolated by conventional methods known to one skilled in the art, such as recrystallization from an organic solvent such as ethyl acetate, methanol, methyl-t-butyl ether and the like, HPLC or flash chromatography.

The compound of formula V is reacted in an acid, such as acetic acid, formic acid, propionic acid, trifluoroacetic acid (TFA), hydrochloric acid or mixtures thereof, preferably formic acid, preferably in the presence of a hydrosilane such as di lower alkyl silane or tri lower alkyl silane, preferably triethylsilane, at a temperature of in the range of about 40° to about 100° C., preferably at about 80° to about 100° C., to form the corresponding compound of formula Ia, wherein $R^{2'}$ is alkyl or aralkyl.

If desired, a compound of formula Ia or a salt thereof, wherein $R^{2'}$ is alkyl or aralkyl, can further be converted to a compound of formula Ib or a salt thereof, wherein $R^{2''}$ is hydrogen, via saponification of the ester by conventional methods, such as reacting the compound of formula Ia or a salt thereof with lithium hydroxide, sodium hydroxide or potassium hydroxide in a solvent such as tetrahydrofuran (THF), dimethylformamide (DMF) or methanol.

The following examples describe the invention in greater detail and are intended to illustrate the invention, but not to limit it.

EXAMPLE 1

Methyl N-[(S)-1-(4-methoxyphenyl)ethyl]-3-amino-3-(3-pyridyl)propanoate

A mixture of methyl nicotinoylacetate (23.6 g, 0.13 mol) and (s)-1-(4-methoxylphenyl)ethylamine(20.0 g, 0.13 mol) was dissolved in toluene (60 mL) to afford a homogeneous solution. Glacial acetic acid (19.5 g, 0.33 mol) was added and resulted in a precipitate formation. The reaction mixture was heated to 62° C. under reduced pressure, the mixture became a clear solution again. The reduced pressure was adjusted to allow the solution to reflux at 62° C. in a steady rate for azeotropic removal of water. The reaction was stopped after 24 h; $^1$H NMR indicated that the reaction was >90% complete. The solvent was evaporated under reduced pressure at 60° C. to afford a brown oil. The crude oil was redissolved in toluene (50 mL) and washed with saturated NaHCO$_3$ solution (2×100 mL) followed by brine (75 mL). The organic layer was separated and evaporated to dryness under vacuum at 60° C. to afford 41.1 of a light brown oil. $^1$H NMR showed that the crude oil contained the desired product, contaminated with 4.3% toluene and 0.86% water by weight. This crude oil was used directly for the subsequent reduction without further purification.

An analytical sample was obtained by recrystallization from ethyl acetate.

MS m/z (rel intensity): 281.20(50), 313.22(MH$^+$, 100), 354.24 (MH$^+$+MeCN, 40), 432.27 (<5).

Elemental analysis, calculated for C$_{18}$H$_{20}$N$_2$O$_3$: C, 69.21; H, 6.45; N, 8.97%. Found: C, 69.27; H, 6.59; N, 8.92%.

EXAMPLE 2

Methyl N-[(S)-1-(4-methoxyphenyl)ethyl]-(S)-3-amino-3-(3-pyridyl)propanoate

The crude methyl N-[(S)-1-(4-methoxyphenyl)ethyl]-3-amino-3-(3-pyridyl)propenoate, (40.6 g, 130 mmol) was dissolved in methanol (200 mL) and mixed with 20% Pd(OH)$_2$/C (4.1 g). The mixture was hydrogenated under atmospheric pressure for 30 h. The mixture was diluted with ethyl acetate (50 mL) and filtered through celite (20 g) to remove the catalyst. The celite was washed with hot (70° C.) ethyl acetate(200 mL). The combined filtrate was concentrated under reduced pressure to near dryness to an oily residue. Crude amine (27.5 g) was dissolved in hot ethyl acetate (40 mL). The resulting hot yellow solution was filtered and rinsed with 15 mL of hot ethyl acetate. The clear solution was concentrated to <50 mL and allowed to stand at room temperature overnight. The resulting white crystalline solid was collected by filtration and washed with cold ethyl acetate (EtOAc) (~15–20 mL), then air dried. Yield of isolated solid: 15.5 g. HPLC analysis showed >99% desired diastereomer. A second crop was obtained from the filtrate after concentration to about 20 mL. Yield: 1.7 g identical by HPLC to first crop; total yield: 17.2 g (62.5%)

White crystalline solid, mp 117.3–119.0° C.

MS(ES$^+$), 315 MH$^+$.

Elemental analysis, calculated for C$_{18}$H$_{22}$N$_2$O$_3$, C, 68.77; H, 7.05; N, 8.91%. Found: C, 68.66; H, 6.95; N, 8.86%.

EXAMPLE 3

Methyl (S)-3-amino-3-(3-pyridyl)propanoate dihydrochloride

A mixture of methyl N-[(S)-1-(4-methoxyphenyl)ethyl)-(S)-3-amino-3-(3-pyridyl)propanoate (57.35 g, 0.148 mol) and triethylsilane (25.81 g, 0.222 mol) in formic acid (120 mL) was heated to 90° C. (oil-bath) while stirring. The initial suspension became a clear solution after 5 minutes at 90° C. Heating and stirring was continued for 2 h. The reaction mixture was cooled to room temperature and the solvent was removed under reduced pressure at 50° C. to give a residual oil. The residual oil was dissolved in ethyl acetate (300 mL) and methanol (100 mL). The solution was filtered. The filtrate was treated slowly with 9.8 M HCl in methanol (30.2 mL, 0.296 mol) with stirring. The resulting solution was diluted with ethyl acetate (200 mL) and heated on a steam-bath to remove excess methanol until the solution became cloudy. The mixture was then stirred at room temperature overnight and the solid product crystallized from the solution. Ethyl acetate (150 mL) was added to the suspension and the mixture was stirred for another 2 h. The solid was collected by filtration and washed with 200 mL of ethyl acetate, then dried in vacu for 1 h. The desired product was obtained as a white powder (27.05 g, 72% yield).

HPLC area purity=98%, ee=99.4%.

mp=197.5–199° C.

A second crop was obtained by concentrating the filtrate and dissolving the residual oil in 200 mL of ethyl acetate and 20 mL of methanol. After seeding, the solution was stirred for 6 h, the second crop was collected by filtration and washed with 100 mL of ethyl acetate, then dried in vacu for 1 h (4.9 g, 13% yield).

Total isolated yield: 31.95 g, 85%.

HPLC area purity=90%, ee=99.8%.

mp=197.5–199.5° C.

MS(EsI) m/z 181.2 (MH$^+$), 222.2 (MH$^+$+MeCN)

Elemental analysis, calculated for: C$_9$H$_{14}$N$_2$O$_2$Cl$_2$: C, 42.71; H, 5.57: N, 11.07; Cl, 28.01. Found: C, 42.68; H, 5.64; N, 11.05; Cl, 28.00.

We claim:
1. A process for preparing a compound of the formula I

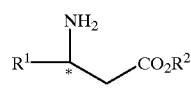

I wherein R$^1$ is aryl, heteroaryl, substituted aryl or substituted heteroaryl and R$^2$ is hydrogen, alkyl or aralkyl, or a salt thereof, comprising reacting a compound of the formula II

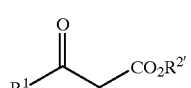

II wherein R$^1$ is as described above and R2 is alkyl or aralkyl, with a compound of the formula III

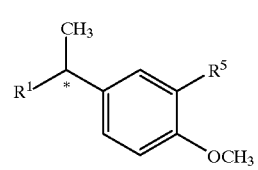

III wherein R5 is hydrogen or alkoxy, under conditions of reduced pressure, such that the reaction solution boils at temperatures of between about 40° and about 65° C., in an inert solvent, which solvent under reduced pressure is capable of azeotropic removal of water, to form the compound of formula IV,

IV

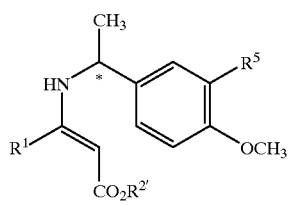

reacting the compound of formula IV with hydrogen gas in the presence of a palladium catalyst to form the compound of formula V

V

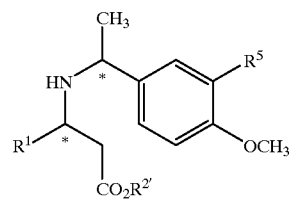

and reacting the compound of formula V to form the compound of formula I.

2. A process of claim 1 wherein the compounds of formula I and III are present in an enantiomeric excess of one enantiomer.

3. A process of claim 2 wherein the compounds of formula I and III are present in an enantiomeric excess of one enantiomer of at least 90% ee.

4. A process of claim 3 wherein the compounds of formula I and III are present in an enantiomeric excess of one of the enantiomers of at least 98% ee.

5. A process of claim 1, wherein $R^1$ is aryl, heteroaryl, mono or di substituted aryl or mono or di substituted heteroaryl, wherein the substituents on the aryl or heteroaryl are independently selected from the group consisting of halogen, hydroxy, lower alkyl, lower alkoxy, lower aralkyl, —$NR^3{}_2$, wherein $R^3$ is a lower alkyl; $R^4$—CONH, wherein $R^4$ is phenyl or a lower alkyl; and —$OC(O)R^6$, wherein $R^6$ is hydrogen, alkyl or aralkyl.

6. A process of claim 5, wherein $R^1$ is phenyl, pyrimidyl, unsubstituted or substituted pyridyl, napthyl or 3,5-dichlorophenyl.

7. A process of claim 6, wherein $R^1$ is 2-pyridyl, 3-pyridyl or 4-pyridyl.

8. A process of claim 7, wherein $R^1$ is 3-pyridyl.

9. A process of claim 1, wherein $R^2$ is a lower alkyl.

10. A process of claim 9, wherein $R^2$ is methyl.

11. A process of claim 1, wherein $R^1$ is 3-pyridyl and $R^2$ is methyl.

12. A process of claim 11 wherein the compounds of formula I and III are present in an enantiomeric excess of one enantiomer of at least 90% ee.

13. A process of claim 11, wherein the inert solvent capable of azeotropic removal of water is xylene, heptane or toluene.

14. A process of claim 13, further comprising reacting the compound of formula II with the compound of formula III to form the compound of formula IV in the presence of at least two equivalents of a carboxylic acid.

15. A process of claim 14, wherein the carboxylic acid is acetic acid.

16. A process of claim 15, further comprising washing the compound of formula IV with an aqueous base to remove excess acid.

17. A process of claim 15, wherein the palladium catalyst is present in an amount of at least 10 weight percent of 20 percent palladium hydroxide on carbon.

18. A process of claim 1, further comprising separating and isolating the compound of formula V into a desired diastereomer.

19. A process of claim 15, further comprising separating and isolating the compound of formula V into a desired diastereomer.

20. A process of claim 15, further comprising reacting the compound of formula V in formic acid, in the presence of a hydrosilane, to form the compound of formula I.

21. A process of claim 1, further comprising reacting the compound of formula V with an acid.

* * * * *

UNITED STATES PATENT AND TRADEMARK OFFICE
CERTIFICATE OF CORRECTION

PATENT NO.   : 6,258,956 B1
DATED        : July 10, 2001
INVENTOR(S)  : Ahmed F. Abdel-Magid, Judith H. Cohen, Cynthia A. Maryanoff, Frank John Vilanni, Jr. and Hua M. Zhong It is certified that error appears in the above-identified patent and that said Letters Patent is hereby corrected as shown below:

<u>Column 8,</u>
Line 50, delete "R2" and change to -- $R^{2'}$ --.
Line 60, delete "R5" and change to -- $R^5$ --.

Signed and Sealed this

Twenty-first Day of May, 2002

Attest:

JAMES E. ROGAN
*Attesting Officer*   *Director of the United States Patent and Trademark Office*